United States Patent
Unsbo

(10) Patent No.: US 7,957,059 B2
(45) Date of Patent: Jun. 7, 2011

(54) DEVICE AND METHOD FOR DEMONSTRATING OPTICAL EFFECTS

(75) Inventor: Jan Peter Unsbo, Älvsjö (SE)

(73) Assignee: Bausch & Lomb Incorporated, Rochester, NY (US)

( * ) Notice: Subject to any disclaimer, the term of this patent is extended or adjusted under 35 U.S.C. 154(b) by 392 days.

(21) Appl. No.: 12/046,054

(22) Filed: Mar. 11, 2008

(65) Prior Publication Data

US 2009/0231693 A1    Sep. 17, 2009

(51) Int. Cl.
G02B 23/00    (2006.01)
G09B 23/22    (2006.01)

(52) U.S. Cl. ........ 359/399; 359/407; 359/662; 434/284; 434/303

(58) Field of Classification Search .................. 359/399, 359/407, 662, 896; 434/284, 300, 303
See application file for complete search history.

(56) References Cited

U.S. PATENT DOCUMENTS

| | | | | |
|---|---|---|---|---|
| 1,521,339 | A | * | 12/1924 | Taylor ........................... 434/303 |
| 2,024,376 | A | | 12/1935 | Lee |
| 3,094,790 | A | * | 6/1963 | Scidmore et al. .............. 434/303 |
| 3,932,949 | A | * | 1/1976 | King .............................. 434/303 |
| D243,761 | S | | 3/1977 | Huckenbeck |
| 4,364,645 | A | | 12/1982 | Feinbloom |
| D275,400 | S | | 9/1984 | Huckenbeck |
| D308,066 | S | | 5/1990 | Huckenbeck |
| 5,815,239 | A | | 9/1998 | Chapman et al. |
| 6,061,189 | A | | 5/2000 | Caplan et al. |
| D484,519 | S | | 12/2003 | Nojima |
| D552,140 | S | | 10/2007 | Tonegawa et al. |
| 2001/0036019 | A1 | | 11/2001 | Fukumoto |
| 2008/0143960 | A1 | * | 6/2008 | MacRae ........................ 351/230 |

FOREIGN PATENT DOCUMENTS

| | | |
|---|---|---|
| GB | 292784 | 6/1928 |
| GB | 817455 | 7/1959 |
| WO | WO 2006/058026 | 6/2006 |

OTHER PUBLICATIONS

Smith, Warren J. "Modern Optical Engineering: The Design of Optical Systems", 1990, McGraw-Hill, p. 73, figure 3.15. Document XP002530155.
Freeman, M.H. et al. "Optics" 2004, Butterworth, Heineman p. 487-490. Document XP009117474.

* cited by examiner

Primary Examiner — Frank G Font
(74) Attorney, Agent, or Firm — John E. Thomas

(57) ABSTRACT

An optical system includes two lens systems, one that provides viewing of an object with relatively no spherical aberration, and another that provides viewing of the object with significant spherical aberration. Preferably, both lens systems provide viewing of the object with relatively no chromatic aberration. The optical system may have the configuration of binoculars.

19 Claims, 3 Drawing Sheets

DEVICE AND METHOD FOR DEMONSTRATING OPTICAL EFFECTS

BACKGROUND OF THE INVENTION

This invention relates to an optical system and device for demonstrating the effect of spherical aberration.

Various binocular devices, including two telescopes connected with a housing, are known. As an example, a conventional pair of binoculars is marked with terminology such as "10×42". In this example, this terminology denotes that the diameter of the objective is $D_o$=42 mm and that the angular magnification is M=10×. It also denotes that the exit pupil (diameter of rays entering the viewer eye) is $D_e$=$D_o$/M=4.2 mm.

In this example of a typical binocular device, the binocular optics includes an objective lens with focal length $f'_o$ and an eyepiece lens with focal length $f'_e$. The objective lens provides a real intermediate image of the distant object in the back focal plane of the objective. The eyepiece lens functions as a simple magnifier that the viewer uses to view the intermediate image. Between the objective lens and eyepiece lens there is typically a prism arrangement to invert the intermediate image so that the final image will not appear upside down to the viewer.

To adjust focus for closer objects or to accommodate for refractive errors of the viewer's eyes, the distance between the objective lens and the eyepiece lens can be adjusted by a wheel that affects the telescopes of both eyes simultaneously. There may also be an individual focus adjustment on the eyepiece of the right telescope, which can be used to compensate for anisometropia of the viewer but also to fine tune defocus in the altered telescope.

The objective lens is usually an achromatic doublet, or possibly an achromatic doublet coupled with a meniscus lens. The achromatic doublet lens is almost free of chromatic aberration, spherical aberration and coma when oriented correctly.

Various contact lenses are commercially available that adjust spherical aberration in order to improve visual acuity of the contact lens wearer. Additional examples of such lenses are described in U.S. Pat. No. 5,815,239 (Chapman et al.). In the illustrated examples in this patent, the optical zone of the contact lenses have a minus aberration value, by matching an appropriate shape factors for the anterior and posterior surfaces of the contact lens optical zones.

SUMMARY OF THE INVENTION

This invention recognized it would be desirable to demonstrate the difference between: vision-correcting ophthalmic lenses, such as contact lenses, that adjust spherical aberration; and such ophthalmic lenses that lack spherical aberration adjustment.

Accordingly, the optical system and device of this invention provides a viewer the opportunity to both: view an object with a relatively large amount of spherical aberration (in order to illustrate vision-correcting ophthalmic lenses lacking spherical aberration adjustment); and view the object with relatively no spherical aberration (in order to illustrate vision-correcting ophthalmic lenses having the spherical aberration adjustment). Since the viewer can view the object with both spherical aberration and without spherical aberration, the viewer can compare easily the effects of spherical aberration to normal vision. The device is relatively simple to use and to manufacture.

According to certain embodiments, this invention includes an optical system comprising: a first lens system that provides viewing of an object with relatively no spherical aberration; and a second lens system that provides viewing of the object with significant spherical aberration.

Preferably, the first lens system and the second lens system each provides viewing of the object with relatively no chromatic aberration, for example, first lens system comprises an achromatic doublet lens, and the second lens system comprises a reversed achromatic doublet lens. The first lens system may include a first telescope comprising an eyepiece lens, and the second lens system may include a second telescope comprising an eyepiece lens, wherein a spacing between the eyepiece lens and the achromatic doublet lens of the first telescope is smaller than a spacing between the eyepiece lens and the reversed achromatic doublet lens of the second telescope.

The first and the second telescopes may be connected with a housing. According to preferred embodiments, the device has the configuration of binoculars. The first and the second telescopes may be mutually adjustable by a viewer to achieve focus of the object at a desired distance. The eyepiece of the second telescope may be adjustable, independently of the eyepiece of the first telescope.

Preferably, the first and second telescopes include exit pupils with the same diameter and/or the first and second telescopes have the same field of view.

According to additional embodiments, this invention includes a method of demonstrating the optical effect of spherical aberration to a viewer, comprising: providing a first lens system that provides viewing of an object with relatively no spherical aberration, and a second lens system that provides viewing of an object with significant spherical aberration; and alternating viewing of an object by the viewer with only the first lens system and only the second lens system.

BRIEF DESCRIPTION OF THE DRAWING FIGURES

FIG. 1 schematically illustrates an embodiment of an optical system of this invention.

Figure 8A:
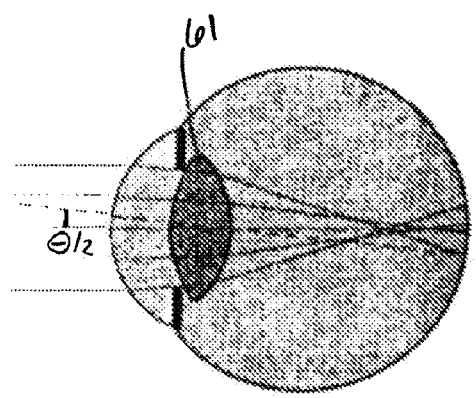

FIG. 8*a* illustrates the optics of a human eye.

Figure 8B:
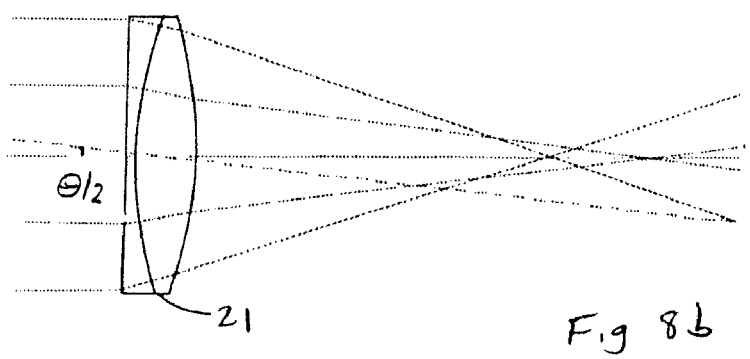

FIG. 8*b* illustrates an achromatic doublet lens.

DETAILED DESCRIPTION OF VARIOUS PREFERRED EMBODIMENTS

Figure 1:
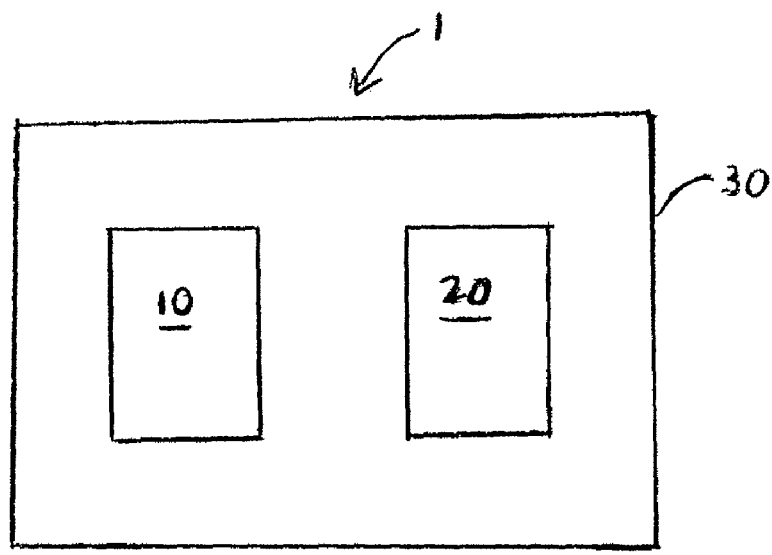
Figure 2:
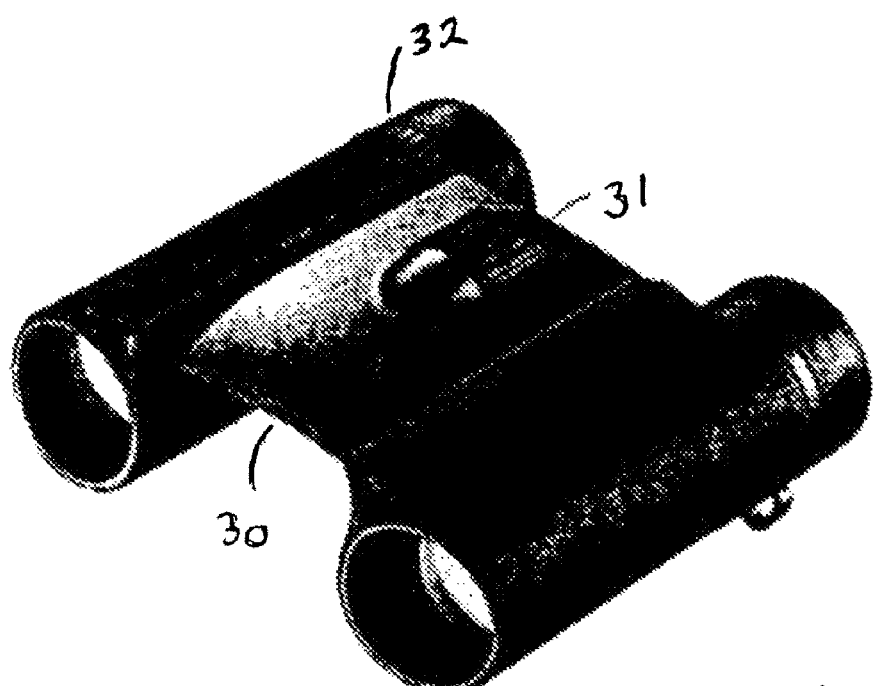
FIG. 2 is a perspective view of an embodiment of a device of this invention.

FIG. 1 illustrates schematically a preferred embodiment of this invention. When a viewer views an object through lens system 10, the object will appear with relatively no spherical aberration (in order to illustrate vision-correcting ophthalmic lenses having the spherical aberration adjustment). When a viewer views an object through lens system 20, the object will appear with a relatively larger amount of spherical aberration (in order to illustrate vision-correcting ophthalmic lenses lacking spherical aberration adjustment). In the illustrated embodiment, lens systems 10 and 20 are supported in a common housing 30, although other configurations are within the scope of the invention. Housing 30 may have the form of a conventional binoculars housing, as illustrated in FIG. 2; in this illustrative example, lens system 10 would be viewed with the right eye (with the left eye closed), and lens system 20 would be viewed with the left eye (with the right eye closed). Of course, the positions of the lens systems could be reversed, if desired.

Figure 3:
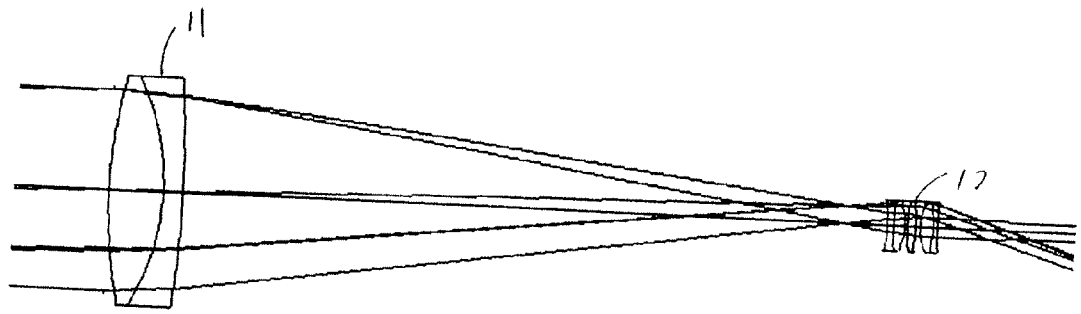
FIG. 3 illustrates an embodiment of a first lens system of this invention.
Figure 4:
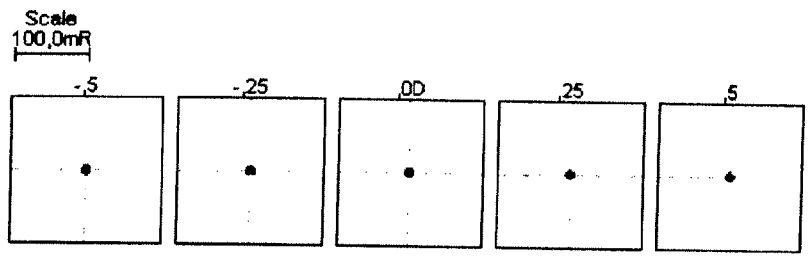
FIG. 4 illustrates viewing of a point source object through the first lens system of FIG. 3, in 0.25 diopter increments.

In the illustrated embodiment, lens system 10 may have the form of a telescope employed in typical binoculars. As illustrated in FIG. 3, lens system 10 includes an objective lens 11 and an eyepiece lens 12. Objective lens 11 is preferably an achromatic doublet lens, as in typical binoculars, as the achromatic lens will impart little chromatic aberration to the viewed object. In the illustrated embodiment, lens system 10 provides 10× magnification. Thus, a viewer looking only through lens system 10 will see an object magnified 10×, but with little spherical and chromatic aberrations, as illustrated schematically in FIG. 4. In the illustrated embodiment, eyepiece lens 12 is a typical eyepiece lens of binoculars. Various binocular eyepieces' lenses are known in the art and may be used in this invention.

Figure 5:
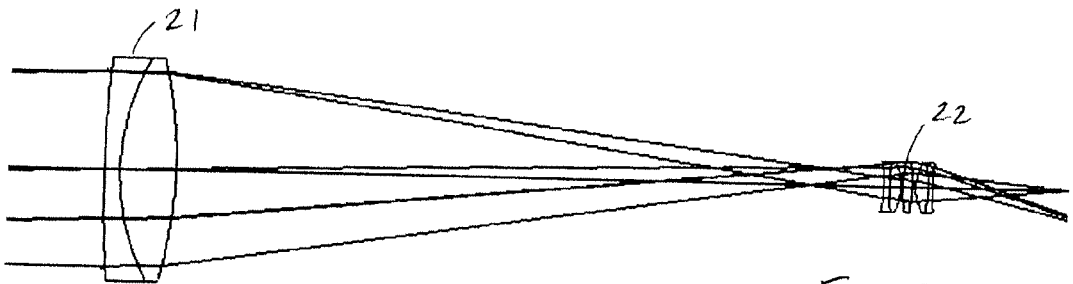
FIG. 5 illustrates an embodiment of a second lens system of this invention.
Figure 6:
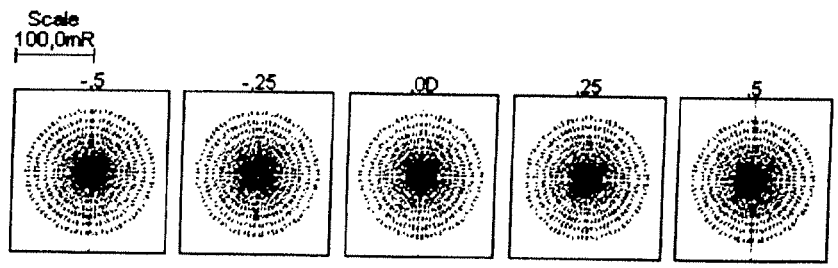
FIG. 6 illustrates viewing of a point source object through the second lens system of FIG. 5, in 0.25 diopter increments.

As illustrated in FIG. 5, lens system 20 includes an objective lens 21 and an eyepiece lens 22. Eyepiece lens 22 is similar to eyepiece lens 21. Objective lens 21 is preferably an achromatic doublet lens, similar to objective lens 11, so that an object is viewed with little chromatic aberration. However, objective lens 21 is a reversed achromatic lens, as compared to objective lens 11. Thus, objective lens 21 will still impart spherical aberration to an object viewed through lens system 20. With this reversed objective lens, in the illustrated embodiment, the viewer will see the object magnified 10×, but with a large degree of superimposed spherical aberration. If the viewer views an object on axis (straight forward) with only the right eye telescope including lens system 20, he will experience almost pure spherical aberration, as illustrated schematically in FIG. 6.

It is noted that the amount of coma present in lens systems 10, 20 may be minimized based on field angle, as discussed in detail below.

According to preferred embodiments, lens system 20 includes a realistic amount of spherical aberration that is magnified, along with the object, when the object is viewed by a viewer of the device. Additionally, lens system 20 should not include significant chromatic aberration or coma, so that the illustrative optical effect is almost purely due to spherical aberration. The objective lens typically used in conventional binoculars, as modified by this invention, serves well the purpose of illustrating spherical aberration because it is generally used at a low f-number and a fairly small object angle. By choosing a telescope with a sufficiently small exit pupil, it is ensured that the pupil of the viewer does not affect the aberration pattern. The amount of spherical aberration in the device is ideally chosen to approximate the amount of spherical aberration in a normal eye multiplied by the magnification of the binoculars to give a realistic, but clearly visible, effect to the viewer.

Figure 7:
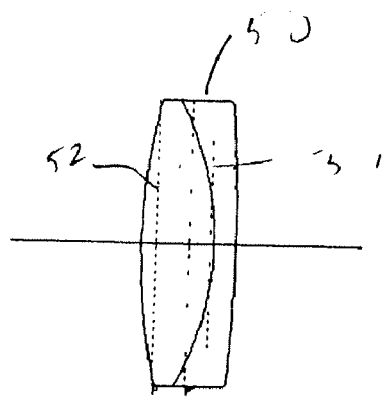
FIG. 7 illustrates an achromatic doublet lens.

When the orientation of the objective, achromatic lens in lens system 20 is reversed, as in FIG. 5, the position of the objective lens with respect to the eyepiece lens may need to different than in lens system 10. The idea is to have a paraxially focused image in the telescope of lens system 20 while having a sharp image in the telescope of lens system 10. The paraxial power of an achromatic doublet lens is the same when the orientation is reversed, but as illustrated in FIG. 7, the principal planes 51, 52 of an achromatic lens 50 are not symmetrical. Thus, if lens system 10 and lens system 20 included objective lenses at the same distance from the eyepiece lens, the back principal plane of objective lens 21 would be much closer to the eyepiece lens 22. In order to achieve a desired focus, the physical distance between the objective lens 21 and eyepiece lens 22 will generally be larger than the distance between objective lens 11 and eyepiece lens 12. For achromatic doublets used in typical commercial binoculars, this increase in spacing between the objective and eyepiece lenses is about 4 to 5 mm.

FIG. 8a illustrates the optics of an average human eye 61, and FIG. 8b illustrates objective lens 21. The wavefront aberration in an eye with pure spherical aberration, adjusted to have paraxial focus on the retina, can be written as $$WA = c_4^0 6\sqrt{5} (\rho/\rho_0)^4,$$

where $c_4^0$ is the Zernike coefficient for spherical aberration, $\rho_0$ is the radius of the pupil and $\rho$ the distance from the pupil centre. To find the angular extent, $\Theta$ (see FIG. 6a), in object space of the transverse aberration pattern on the retina, one uses $$\theta/2 = \frac{dWA}{d\rho}(\rho_0) = 24\sqrt{5}\frac{c_4^0}{\rho_0}.$$

The Zernike coefficient for spherical aberration ($Z_4^0$) for a 6 mm pupil size is 0.15 μm in the average human eye. For the average eye one finds $\Theta = 0.0054$ rad.

Lens system 20 should, in a realistic way, show the viewer how the spherical aberration in the average human eye affects the image quality. This means that the angular extent in object space, $\Theta$, of the spherical aberration in lens 21 (FIG. 8b) should match that of the average eye (FIG. 8a). The effect of spherical aberration in lens system 20 on the object scene will then be the same as in the average human eye, but the viewer will see the scene magnified through the telescope.

Accordingly, it is preferred that the f-number and/or design of the achromatic doublet in the binoculars is chosen such that $\Theta$ approximates 0.0054 rad, for the reversed achromatic lens 21. This can be verified easily by imaging two adjacent laser spots on a wall through the lens system 20. With the focus adjusted for paraxial rays, the circular halos (transverse aberration pattern) should be just in contact when the angular distance between the spots is 0.0054 rad.

It has been found that the f-number (focal length/diameter) for the achromatic doublet lens in typical commercial binoculars is around f/3. If such a lens is just reversed, in constructing lens system 20, the spherical aberration will generally be too large. Instead, the lens will be have to be stopped down to about f/4 to f/4.5 in order to have $\Theta = 0.0054$ rad. The correct f-number for any specific objective lens may vary depending on its design, and can be determined by one skilled in the art.

The angular magnification of a pair of binoculars is given by $M = f_o/f_e$. The spherical aberration effect on the object seen through lens system 21 will be that of an average eye, but the object and spherical aberration will be magnified M times. To clearly demonstrate the effect of spherical aberration the magnification should be fairly large. It was determined that an angular magnification of 10 worked well, but other angular magnification levels may be suitable. However, a too high magnification level will make it hard to steady the image while a viewer holds the binoculars. In contrast, an object seen through lens system 11 will be magnified M times, but without magnification of spherical aberration.

The diameter of the rays entering the eye of the viewer (exit pupil diameter) should be smaller than the pupil of the viewer. This is important, because otherwise the size and shape of the viewer's pupil will affect the aberration pattern seen through lens system 20. When some part of the exit pupil falls outside the eye's pupil, rays are lost and, for example, halos seen around point sources through lens system 20 will not be symmetric. This effect is very confusing, and since this effect has little to do with spherical aberration, it should be minimized. In order to avoid the confusing ray cut-off, the exit pupil should be fairly small, for example, no greater than 3 mm, and preferably less than 2 mm. It is noted that retinal illumination is proportional to pupil area, so a too small exit pupil will make a scene look dim. In selecting an exit pupil size, some compromise may be required in designing the lens systems, balancing potential use of the device in both bright environments, when the viewer's pupil will be small, and dim environments, when the viewer's pupil will be large. It is preferred that the exit pupil is the same in both lens systems 10 and 20.

If it was desired to customize the device based on potential viewing conditions, then two versions of the device could be considered: binoculars comprising lens systems 10 and 20 and with a small exit pupil (for example, 2 mm or smaller) that works well in a bright environment; and binoculars comprising lens systems 10 and 20 and with a larger exit pupil (for example 3 mm) that works better in a darker environment.

The field of view in a pair of commercial binoculars with 10× magnification may be as large as 6.5°. At 3.25° field angle through the reversed achromatic doublet of lens system 21, there will then be some amount of coma. It is important that there is not too much coma with appreciably worse image quality in the peripheral field of view. The amount of coma in any specific reversed achromatic doublet is often dependent on how the actual lens was manufactured and/or designed. One reversed achromatic doublet lens tested showed a relatively high amount of coma at 3.25° field angle, while in another tested reversed achromatic doublet lens, the amount of coma was not appreciable. The field of view (and thus the amount of visible coma) can be reduced by introducing an extra field stop in the plane of the intermediate image, if necessary. However, the field of view should be kept as large as possible for comfort reasons, and should only be reduced if necessary. Nonetheless, it is preferred that the field of view is the same in both lens systems 10 and 20.

As mentioned, in a preferred embodiment, the device may be housed in a conventional binoculars housing 30. The binoculars preferably include a conventional main focus adjustor 31, allowing a viewer to focus the lens systems. In operation, the view would first adjust the main focus wheel 31 of the binoculars while viewing through lens system 10 only (which, in the illustrative example, corresponds to the left eye, sharp vision). Then the viewer views the scene alternating between the left and right eye, in order to compare the viewed object with and without spherical aberration. If the device is used to view an object at a distance, such as a visual acuity chart, the viewer will experience the reduced contrast typical of spherical aberration. In a dark scene, with bright light sources, the viewer may experience halos typical in night driving. The individual focus correction 32 on lens system 20 should be in the default position if the viewer does not have large anisometropia.

The device may include a calibration ring fitted onto objective lens 21 of lens system 20, in order to reduce the aperture size.

The individual focus on eye piece 22 may be calibrated as follows. Place a plate with a small hole (about ⅓ of the lens diameter) in front of the objective lens 21. View an object through lens system 10. Adjust the main focus wheel to achieve a sharp image. Then view the same object with lens system 20. Adjust the individual defocus on eyepiece 22 to achieve the optimum image. In essence, this procedure should place the paraxial image in lens system 20 in focus when the image in lens system 10 is sharp.

It will be appreciated that the preferred, illustrative embodiment employs a conventional binoculars housing with two telescopes. One telescope may have the form of a conventional binoculars telescope. The second telescope incorporates the reversed achromatic objective lens, in place of a conventional binocular objective lens, and the distance between the objective lens and the eyepiece lens is modified, as described herein. Adjustments to the exit pupil size may be desired in some cases, as described herein.

A device was constructed by modifying one of the telescopes of a conventional 10×42 (6.5°) binoculars:
Diameter of objective $D_o$=42 mm
Angular magnification M=10×
Field of view at 10× magnification–6.5°
Objective lens–achromatic doublet+meniscus lens
Objective lens in modified telescope–reversed achromatic doublet+meniscus lens
Focal length of achromatic doublet: 120 mm
f-number of achromatic doublet (original): f/2.9
f-number of achromatic doublet in modified telescope: f/4
Exit pupil: 3 mm
Calculated shift in distance between objective and eyepiece for modified telescope–approximately 5 mm
Actual implemented shift in distance between objective and eyepiece for modified telescope–3.5 mm (remaining shift can be accommodated by adjusting individual focus adjustment 32 on the eyepiece of the modified telescope)

This prototype worked well to demonstrate the differences in optical effects attributed to spherical aberration. However, due to the relatively large exit pupil, non-symmetric halos appeared if the viewer's pupil was misaligned with the instrument. There was also a noticeable amount of coma.

A second device was constructed by modifying one of the telescopes of a conventional 10×25 (6.5°) binoculars:
Diameter of objective $D_o$=25 mm
Angular magnification M=10×
Field of view at 10× magnification–6.5°
Objective lens–achromatic doublet
Objective lens in modified telescope–reversed achromatic doublet
Focal length of achromatic doublet: 78 mm
f-number of achromatic doublet (original): f/3.1
f-number of achromatic doublet in modified telescope: f/4.5
Exit pupil: 1.7 mm
Calculated shift in distance between objective and eyepiece for modified telescope–approximately 4.5 mm
Actual implemented shift in distance between objective and eyepiece for modified telescope–4 mm (remaining shift can be accommodated by adjusting individual focus adjustment 32 on the eyepiece of the modified telescope)

This prototype worked well to demonstrate the differences in optical effects attributed to spherical aberration. The appearance of non-symmetric halos was much less noticeable in this second device due to the smaller exit pupil. This device was not seriously affected by coma, even with the full field of view. However, a dark scene will appear relatively darker due to the small exit pupil.

While there are shown and described herein certain specific illustrative embodiments and structures for the present invention, it will be apparent to those skilled in the art that various modifications may be made without departing from the spirit and scope of the underlying inventive concept and that the same is not limited to particular structures shown herein and described except as indicated by the scope of the appended claims.

We claim:

1. An optical system comprising:
a first lens system that provides viewing of an object with relatively no spherical aberration and with relatively no chromatic aberration, the first lens system comprising an achromatic doublet lens; and
a second lens system that provides viewing of the object with significant spherical aberration and with relatively no chromatic aberration, the second lens system comprising a reversed achromatic doublet lens that imparts spherical aberration,
wherein the effect of spherical aberration and the object are magnified by the second lens system.

2. The optical system of claim 1, wherein the first lens system includes a first telescope comprising an eyepiece lens, and the second lens system includes a second telescope comprising an eyepiece lens.

3. The optical system of claim 2, wherein a spacing between the eyepiece lens and the achromatic doublet lens of the first telescope is smaller than a spacing between the eyepiece lens and the reversed achromatic doublet lens of the second telescope.

4. The optical system of claim 2, wherein the first and second telescopes are connected with a housing.

5. The optical system of claim 4, wherein the first and the second telescopes are mutually adjustable by a viewer to achieve focus of the object at a desired distance.

6. The optical system of claim 5, wherein the eyepiece of the second telescope is adjustable, independently of the eyepiece of the first telescope.

7. The optical system of claim 2, wherein the first and second telescopes include exit pupils with the same diameter.

8. The optical system of claim 2, wherein the first and second telescopes have the same field of view.

9. The optical system of claim 1, wherein the first lens system includes a first telescope comprising a first objective lens and a first eyepiece lens, and the second lens system includes a second telescope comprising a second objective lens and a second eyepiece lens, and the first telescope and the second telescope each provides view of the object with relatively no chromatic aberration.

10. The optical system of claim 9, wherein the first objective lens comprises an achromatic doublet lens, and the second objective lens comprises a reversed achromatic doublet lens, and a spacing between the eyepiece lens and the achromatic doublet lens of the first telescope is smaller than a spacing between the eyepiece lens and the reversed achromatic doublet lens of the second telescope.

11. The optical system of claim 9, wherein the first and second telescopes include exit pupils with the same diameter, and have the same field of view.

12. The optical system of claim 9, wherein the first and second telescopes are connected with a housing.

13. The optical system of claim 12, having the configuration of binoculars.

14. The optical system of claim 1, wherein an angular extent in object space of the spherical aberration in the second lens system matches that of an average human eye.

15. A method of demonstrating the optical effect of spherical aberration to a viewer, comprising:
providing a first lens system that provides viewing of an object with relatively no spherical aberration and with relatively no chromatic aberration, and a second lens system that provides viewing of an object with significant spherical aberration and with relatively no chromatic aberration, the second lens system comprising a reversed achromatic doublet lens that imparts spherical aberration, and wherein the spherical aberration effect is magnified, along with the object, when the object is viewed by the second lens system; and
alternating viewing of an object by the viewer with only the first lens system and only the second lens system.

16. The method of claim 15, wherein the first lens system includes a first telescope comprising a first objective lens and a first eyepiece lens, and the second lens system includes a second telescope comprising a second objective lens and a second eyepiece lens.

17. The method of claim 16, wherein the first objective lens comprises an achromatic doublet lens, and the second objective lens comprises a reversed achromatic doublet lens, and a spacing between the eyepiece lens and the achromatic doublet lens of the first telescope is smaller than a spacing between the eyepiece lens and the reversed achromatic doublet lens of the second telescope.

18. The method of claim 16, wherein the first and the second telescopes include exit pupils with the same diameter, and have the same field of view.

19. The method of claim 18, wherein the first and the second telescopes are connected with a housing, and the device has the configuration of binoculars.

* * * * *